United States Patent
Walshe et al.

(10) Patent No.: US 6,906,184 B1
(45) Date of Patent: Jun. 14, 2005

(54) PROCESS FOR ANTIPARASITIC AGENT

(75) Inventors: Nigel D. Walshe, Sandwich (GB);
Selena J. Cambers, Sandwich (GB)

(73) Assignee: Pifzer, Inc., New York, NY (US)

( * ) Notice: Subject to any disclaimer, the term of this patent is extended or adjusted under 35 U.S.C. 154(b) by 0 days.

(21) Appl. No.: 10/203,869

(22) PCT Filed: Jul. 23, 1998

(86) PCT No.: PCT/EP98/04931

§ 371 (c)(1),
(2), (4) Date: Apr. 28, 2003

(87) PCT Pub. No.: WO99/07721

PCT Pub. Date: Feb. 18, 1999

(30) Foreign Application Priority Data

Aug. 5, 1997 (GB) .............................................. 9716567

(51) Int. Cl.$^7$ ............................ C07H 1/00; C07H 17/08
(52) U.S. Cl. ...................................... 536/7.1; 536/18.5

(58) Field of Search .................................. 536/7.1, 18.5; 514/30

(56) References Cited

U.S. PATENT DOCUMENTS 5,962,659 A * 10/1999 Baker et al. .................. 536/7.1

FOREIGN PATENT DOCUMENTS

| EP | 0379341 A2 | | 7/1990 |
| WO | WO 94/15944 | * | 7/1994 |
| WO | WO 95/10525 | | 4/1995 |

* cited by examiner

Primary Examiner—Elli Peselev
(74) Attorney, Agent, or Firm—Peter Richardson; Thomas A. Wootton; Mary J. Hosley

(57) ABSTRACT

An improved process for the preparation of the antiparasitic compound 25-cyclohexyl-22,23-dihydro-5-hydroxyiminoavermectin B1 monosaccharide from doramectine and intermediates therefor and crystalline solvates thereof.

5 Claims, No Drawings

PROCESS FOR ANTIPARASITIC AGENT

This application is a national phase under 35 U.S.C. § 371 of PCT/EP98/04931, international filing date of Jul. 23, 1998, which claims priority to GB 9716567.4, filed Aug. 5, 1997.

This invention relates to an improved process for the preparation of an antiparasitic agent derived from doramectin, and intermediates therefor.

Doramectin is a widely employed fermentation derived antiparasitic agent, active against a wide variety of nematode and arthropod parasites in sheep and cattle. According to the specification of our International patent application WO 94/15944 we describe and claim a variety of avermectin 5-oxime monosaccharide derivatives including the compound 25-cyclohexyl-22,23-dihydro-5-hydroxyiminoavermectin B1 monosaccharide (named in that application as 5-oximino-22,23-dihydro-25-cyclohexylavermectin B1 monosaccharide) derived from doramectin. This compound has been found to have exceptional activity against fleas and heartworm combined with low toxicity which makes it particularly valuable for use in domestic animals such as cats and dogs.

As described in our earlier application, this compound is prepared from doramectin by a process which involves firstly hydrogenation to give 25-cyclohexyl-22,23-dihydroavermectin B1, followed by mild acid treatment to hydrolyse one of the C-13 α-oleandrosyl groups to give the corresponding monosaccharide derivative. This product is then oxidised to give the 5-oxo derivative which is finally reacted with hydroxylamine hydrochloride to yield the 5-oxime.

However, like most of the avermectins, all of the intermediates involved in this process are obtained as gums or amorphous solids which require purification by chromatography and the process is thus not readily amenable to scale-up. We have now surprisingly discovered that by performing the reaction sequence in a different order, with the hydrogenation and oxidation steps performed first, the resulting novel intermediate, (25S)-25-cyclohexyl-5-demethoxy-25-de(1-methylpropyl)-22,23-dihydro-5-oxoavermectin A1a (25-cyclohexyl-22,23-dihydro-5-oxoavermectin B1) can be crystallised from an aqueous lower alkanol such as methanol or isopropanol and this greatly facilitates the isolation and purification of this intermediate. We have further discovered that reaction of this intermediate with hydroxylamine hydrochloride to give the 5-oxime and the hydrolysis step to give the monosaccharide derivative may be performed as a single concurrent reaction and this further improvement reduces the number of individual steps in the process which reduces handling and isolation steps leading to an improvement in the overall yield and quality of the final product. Moreover we have now unexpectedly discovered that the final product can itself be recrystallised from a range of organic solvents, including in particular toluene or methanol and this forms a further aspect of the present invention.

The nomenclature used in the present application is adapted from that used for the avermectins. Thus the symbols A and B are used to designate a methoxy or hydroxy group at the 5-position respectively; the numeral 1 is used to designate a double bond at the C-22,23 position and 2 to designate the absence of the double bond and presence of a C-23 hydroxy group; and the symbols a and b indicate a sec-butyl or iso-propyl group at the C-25 position respectively. Thus the chemical name for doramectin is 25(R)-25-cyclohexyl-5-O-demethyl-25-de(1-methylpropyl) avermectin A1a, although it is more generally described in the previous publications as 25-cyclohexyl avermectin B1. Similarly the compound -25-cyclohexyl-22,23-dihydro-5-hydroxyiminoavermectin B1 monosaccharide is more correctly referred to as (5Z, 25S)-25-cyclohexyl-4'-O-de(2,6-dideoxy-3-O-methyl-α-L-arabino-hexopyranosyl)-5-demethoxy-25-de(1-methylpropyl)-22,23-dihydro-5-hydroxyiminoavermectin A1a. For the sake of clarity and brevity the short form of nomenclature will continue to be used in the present specification although both names are included in the experimental section.

According to the present invention the overall process for preparing 25-cyclohexyl-22,23-dihydro-5-hydroyximinoavermectin B1 monosaccharide comprises the steps of:

(i) catalytic hydrogenation of doramectin in an organic solvent to yield 25-cyclohexyl-22,23-dihydroavermectin B1.

(ii) oxidising the above product with manganese dioxide in an organic solvent to yield 25-cyclohexyl-22,23-dihydro-5-oxoavermectin B1 and if desired crystallising the product.

(iii) reacting the above product with hydroxylamine hydrochloride in an aqueous organic solvent.

(iv) optionally crystallising the product from toluene and/or methanol.

The novel intermediate 25-cyclohexyl-22,23-dihydro-5-oxoavermectin B1 is also active in its own right as an antiparasitic agent as well as being a key intermediate in the present process.

The process is shown in the following reaction scheme:

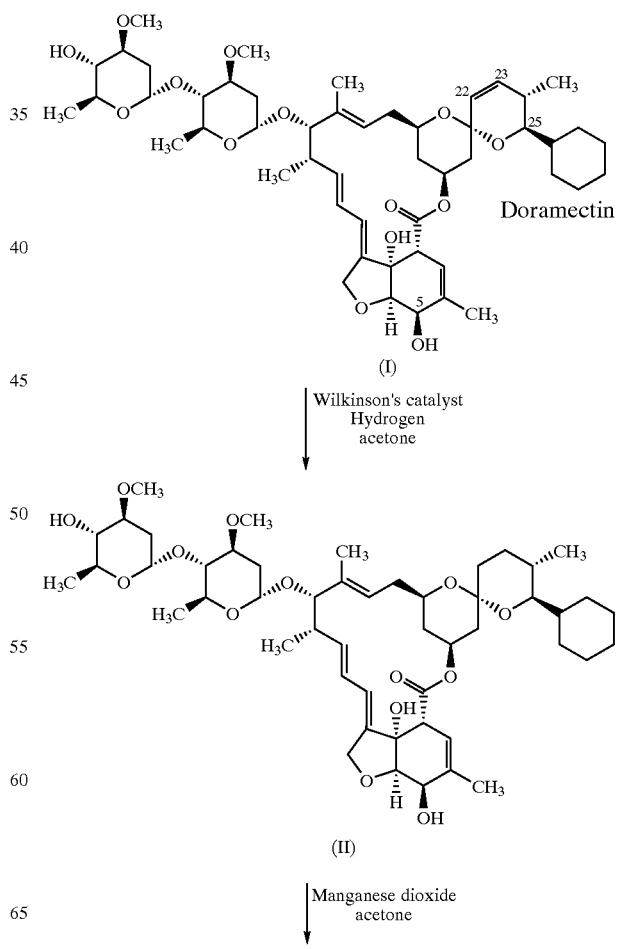

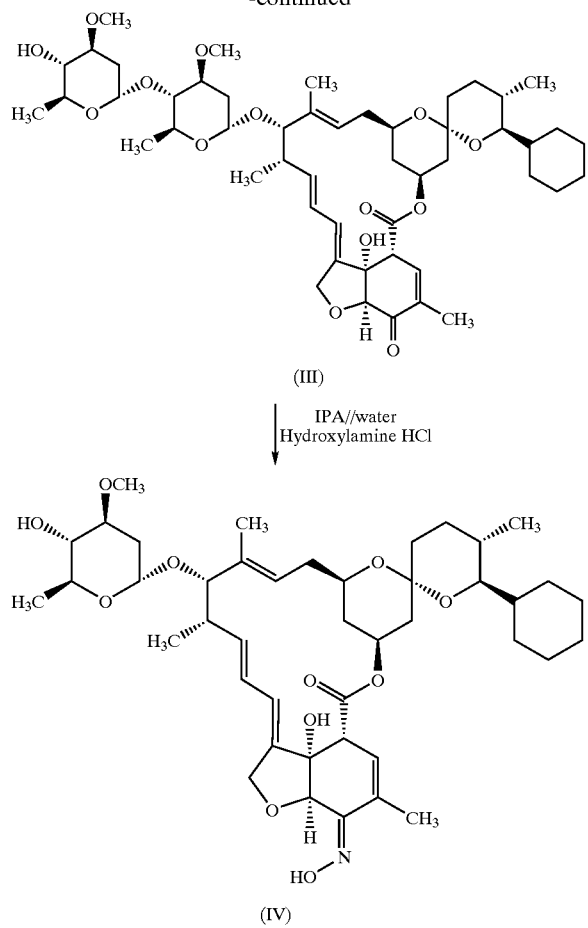

(III)

IPA//water
Hydroxylamine HCl (IV)

The first step in the above process is generally performed using acetone as solvent and using Wilkinson's catalyst (tris(triphenylphosphine)rhodium (1) chloride). Hydrogenation is effected at a pressure of 3 to 4 bar and is generally complete after a period of 6–10 hours at 20–30° C. The product (II) is isolated by filtration and removal of the solvent.

The oxidation step is again generally performed in acetone in the presence of manganese dioxide at room temperature but other organic solvents may also be used. Reaction is generally complete after 1 to 3 hours and the reaction mixture is filtered, the solvent replaced by isopropanol or methanol under reflux and water added. On cooling 25-cyclohexyl-22,23-dihydro-5-oxoavermectin B1 (III) crystallises from solution and is collected and dried.

The final step of the process is performed by treating the above 5-oxo intermediate with hydroxylamine hydrochloride. The reaction is generally performed in aqueous isopropanol at a temperature of from 30° C. to reflux temperature, preferably at 40–50° C. Formation of the 5-oxime and hydrolysis of the terminal C-13 saccharide group proceed concurrently and the reaction is monitored, for example by high pressure liquid chromatography, until complete. Water immiscible organic solvents, e.g. toluene and t-butyl methyl ether are added, the organic layer washed, typically with dilute sodium bicarbonate and brine, dried if needed and the solvent removed. The crude product can be further purified by crystallisation from toluene and is obtained as a variable solvate which collapses to an amorphous powder on drying under vacuum. Alternatively the product (IV) is crystallised or recrystallised from methanol and is obtained as a white crystalline solid, again as a variable methanol/water solvate.

The following Examples illustrate the process of the present invention. the preparation of the intermediate 25-cyclohexyl-22,23-dihydro-5-oxoavermectin B1 and its use in the preparation of 25-cyclohexyl-22,23-dihydro-5-hydroxyimino-avermectin B1 monosaccharide. Yields are quoted based on the activity of the doramectin starting material, and of the product.

EXAMPLE 1

(25S)-25-Cyclohexyl-5-O-demethyl-25-de(1-methylpropyl)-22,23-dihydroavermectin A1a: [25-cyclohexyl-22,23-dihydroavermectin B1]

(25R)-25-Cyclohexyl-5-O-demethyl-25-de(1-methylpropyl)avermectin A1a (doramectin) (500 g) was dissolved in acetone (2500 ml). The solution was charged to a 5 liter stainless steel Buchi hydrogenator and purged with nitrogen. Wilkinson's catalyst (tris(triphenylphosphine)rhodium (I) chloride) (9.5 g) was added and the reaction hydrogenated at 3.45 bar (50 psi) hydrogen pressure at room temperature. After 8 hours, the reaction was complete and the reaction mixture was filtered to remove insolubles. The resulting liquor was concentrated to dryness under vacuum and the resulting brown foam washed with acetonitrile and oven-dried at 50° C. under vacuum to yield the title product as a cream solid (416 g, 90%).

EXAMPLE 2

(25S)-25-cyclohexyl-5-demethoxy-25-de(1-methylpropyl)-22,23-dihydro-5-oxo-avermectin A1a: [25-cyclohexyl-22,23-dihydro-5-oxoavermectin B1]

(25S)-25-cyclohexyl-5-O-demethyl-25-de(1-methylpropyl)-22,23-dihydroavermectin A1a (200 g) was dissolved in acetone (1600 ml). Activated manganese dioxide (483 g) was added and the resulting slurry stirred at room temperature. After 1–2 hours, the reaction was complete and the mixture was filtered through a clarcel pad to remove the manganese dioxide.

The resulting filtration liquor was distilled to low volume, then isopropyl alcohol was added and distillation continued (adding more isopropyl alcohol as and when necessary) until the reflux temperature was 82° C. (equivalent to the boiling point of isopropyl alcohol). The reaction volume was then adjusted to 700 ml, by further distillation, or by adding additional isopropyl alcohol, and reflux stopped. Water (7 ml) was added and the reaction allowed to cool to room temperature, whereupon the product crystallised from solution. This was granulated overnight at room temperature, the product collected by filtration, washed with isopropyl alcohol and oven dried at 50° C. under vacuum to yield the title product as a pale yellow solid(152.5 g, 81.3%).

H.P.L.C: Novapak (trade mark) C18, 150 mm–3.9mm column, mobile phase acitonitrile, water (80:20 v/v), flow rate 1.0 ml/minute, retention time 19 minutes.

M.S: (positive ion electrospray) $MNa^+$=923.3.

N.M.R: spectrum fully consistent with the assigned structure.

EXAMPLE 3

(5Z,25S)-25-cyclohexyl-4'-O-de(2,6-dideoxy-3-O-methyl-α-L-arabino-hexopyranosyl)-5-demethoxy-25-de(1-methylpropyl)-22,23-dihydro-5-hydroxyimino-avermectin A1a: [25-cyclohexyl-22,23-dihydro-5-hydroxyimino-avermectin B1 monosaccharide].

(25S)-25-cyclohexyl-5-demethoxy-25-de(1-methylpropyl)-22,23-dihydro-5-oxo-avermectin A1a (15 g)

was stirred with isopropyl alcohol (120 ml) and water (15 ml) to give a pale yellow slurry. Hydroxylamine hydrochloride (4.67 g) was added and the reaction heated to 40–45° C., whereupon a solution formed. After 14 hours. the reaction was complete and was allowed to cool to room temperature, tert-butyl methyl ether (60 ml), toluene (60 ml) and water (30 ml) were added and the reaction stirred well. The layers were then allowed to separate and the resulting organic layer was washed with 5% w/v aqueous sodium bicarbonate solution (60 ml) and then 20% w/v brine solution (60 ml). The final organic layer was distilled to low volume and toluene added. The distillation was continued (adding more toluene as and when necessary) until the reflux temperature was 111° C. (boiling point of toluene). The reaction volume was then adjusted to 120 ml by further distillation, or by adding additional toluene and the reaction was then allowed to cool to room temperature and the desired product crystallised from solution. This was granulated overnight at room temperature, the product collected by filtration and washed with toluene, to yield the final product, a crystalline solid, as a toluene solvate of variable stoicheometry. The product was dried under vacuum at 50° C. to yield the title product as a white amorphous powder (9.9 g, 77%).

Alternative Recrystallisation of (5Z,25S)-25-cyclohexyl)-4'-O-de(2,6-dideoxy-3-O-methyl-α-L-arabinohexopyranosyl)-5-demethoxy-25-de(1-methylpropyl)-22,23-dihydro-5-hydroxyiminoavermectin A1a The process is the same as above as far as the isolation of the toluene crystallised material. In the alternative process this solid is not oven dried, but is dissolved in methanol.

Toluene-crystallised solid (121 g) was dissolved in methanol (525 ml) and heated to reflux. Solvent was removed by distillation until the product started to crystallise from solution. The reaction mixture was allowed to cool to below the reflux temperature and water (31 ml) added. The solution was then allowed to cool to room temperature to allow crystallisation and allowed to granulate overnight. The product was collected by filtration, washed with methanol and oven dried at 50° C. under vacuum to yield the title product as a white, crystalline solid. (88.159 g, 68.6%). The product was obtained as a methanol/water solvate of variable stoicheometry.

What is claimed is:

1. A process for the preparation of 25-cyclohexyl-22,23-dihydro-5-oxoavermectin B1 which comprises oxidising 25-cyclohexyl-22,23-dihydroavermectin B1.

wherein said process is performed with manganese dioxide in an organic solvent, wherein the solvent is acetone.

2. Crystalline 25-cyclohexyl-22,23-dihydro-5-hydroxyiminoavermectin B1 toluene solvate obtained by recrystallising 25-cyclohexyl-22,23-dihydro-5-hydroxyiminoavermectin B1 monosaccharide from toluene.

3. Crystalline 25-cyclohexyl-22,23-dihydro-5-hydroxyiminoavermectin B1 monosaccharide methanol and water solvate obtained by crystallising 25-cyclohexyl-22,23-dihydro-5-hydroxyiminoavermectin B1 monosaccharide from aqueous methanol.

4. A process for the preparation of 25-cyclohexyl-22,23-dihydro-5-hydroximinoavermectin B1 monosaccharide which comprises reacting 25-cyclohexyl-22,23-dihydro-5-oxoavermectin B1 with hydroxylamine hydrochloride in aqueous isopropyl alcohol, wherein the product is crystallised from any of: toluene, methanol, and mixtures thereof.

5. A process for the preparation of 25-cyclohexyl-22,23-dihydro-5-hydroximinoavermectin B1 monosaccharide which comprises reacting 25-cyclohexyl-22,23-dihydro-5-oxoavermectin B1 with hydroxylamine hydrochloride in aqueous isopropyl alcohol, wherein the process is performed at a temperature of from 40–50° C., wherein the product is crystallised from any of toluene, methanol, and mixtures thereof.

* * * * *